United States Patent [19]

Dasinger

[11] Patent Number: 5,153,320

[45] Date of Patent: Oct. 6, 1992

[54] HETEROPOLYSACCHARIDE 105-4

[75] Inventor: Bruce L. Dasinger, Niantic, Conn.

[73] Assignee: Pfizer Inc., New York, N.Y.

[21] Appl. No.: 384,939

[22] Filed: Jul. 25, 1989

[51] Int. Cl.$^5$ .................. C08B 37/00; C07H 1/00; C07H 3/00

[52] U.S. Cl. .................. 536/123; 536/114; 536/1.1; 536/55.1; 435/101; 435/104

[58] Field of Search ........... 536/123, 114, 1.1, 55.1; 435/101, 104

[56] References Cited

U.S. PATENT DOCUMENTS

| | | | |
|---|---|---|---|
| 4,233,438 | 11/1980 | Myers et al. | 536/123 |
| 4,401,760 | 8/1985 | Peik | 435/101 |
| 4,454,316 | 6/1986 | Veeder et al. | 536/123 |
| 4,634,667 | 7/1987 | Linton et al. | 435/101 |
| 4,689,160 | 8/1987 | Steenberger et al. | 536/114 |

OTHER PUBLICATIONS

Gherna et al., ATCC Catalogue of Bacteria and Phages, 17th ed., 1989, pp. 165–182.

Bergey's Manual of Systematic Bacteriology, vol. 1, pp. 161–199.

*Primary Examiner*—Ronald W. Griffin
*Assistant Examiner*—Pamela S. Webber
*Attorney, Agent, or Firm*—Peter C. Richardson; Paul H. Ginsburg; Robert F. Sheyka

[57] ABSTRACT

Heteropolysaccharide 105-4, prepared by fermentation of a new unnamed Pseudomonas species ATCC 53923 is useful as an industrial thickening, suspending or stabilizing agent.

5 Claims, 1 Drawing Sheet ns ATCC 53923 is composed principally of carbohy-
HETEROPOLYSACCHARIDE 105-4

BACKGROUND OF THE INVENTION

This invention pertains to the field of microbial polysaccharides. In particular, the polysaccharides of interest occur in the form of exocellular heteropolysaccharides which are high molecular weight, generally linear or branched, carbohydrates containing two or more different kinds of monosaccharides that form repeating units that are polymerized.

These heteropolysaccharides are widely used in agriculture and a variety of industrial applications, including food, well drilling, paint, etc. Commercial demand for these heteropolysaccharides continues to increase.

One of the most widely used heteropolysaccharides is xanthan, or xanthan gum, which is produced during fermentation by bacteria of the genus Xanthomonas, typically *Xanthomonas camoestris*. This xanthan heteropolysaccharide contain glucose, mannose and glucuronic acid. Various industrial uses of xanthan gum are known, see e.g. U.S. Pat. Nos. 3,326,305, and 4,244,826.

Another widely useful class of heteropolysaccharides are the succinoglycans, a class of exocellular heteropolysaccharides produced by bacteria of the genera Alcalioenes, Aorobacterium and Pseudomonas. These succinoglycans contain galactose, glucose and variable proportions of acid residues such as pyruvate, succinate and acetate. Industrial uses for these succinoglycans are also known, see e.g., European Patent Office Application No. 040445, and U.S. Pat. Nos. 4,339,239, 4,347,289, and 4,298,795.

SUMMARY OF THE INVENTION

Figure 1:
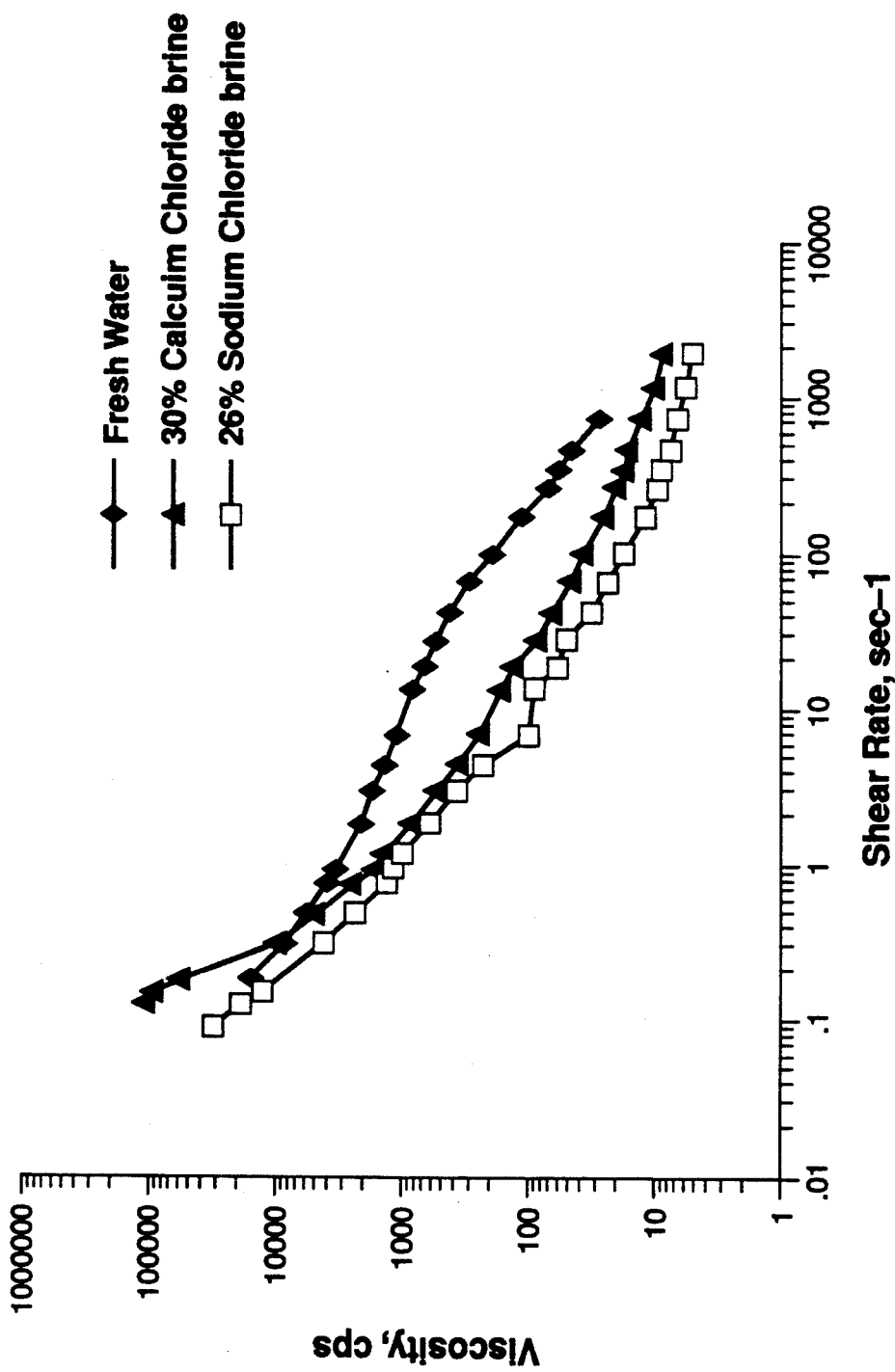
FIG. 1 illustrates the viscosity of 105-4 in various solutions.

The present invention comprises a heteropolysaccharide designated 105-4, said polysaccharide containing mannose, galactose and glucose in the approximate molar ratio of 1.3:1:3.6, said polysaccharide also containing, based on the weight of the polysaccharide, from about 10 to about 25% by weight uronic acid and from about 10 to about 15% by weight acetate groups.

In a further embodiment, the present invention comprises a heteropolysaccharide produced by a Pseudomonas species ATCC 53923 and designated 105-4; said polysaccharide containing mannose, galactose and glucose in the approximate molar ratio of 1.3:1:3.6, said polysaccharide also containing, based on the weight of the polysaccharide, from about 10 to about 25% by weight uronic acid and from about 10 to about 15% by weight acetate groups.

The present invention also comprises a process for preparing a heteropolysaccharide containing mannose, galactose and glucose in the approximate molar ratio of 1.3:1:3.6, said polysaccharide also containing, based on the weight of the polysaccharide, from about 10% to about 25% by weight uronic acid and about 10 to about 15% by weight acetate groups comprising growing Pseudomonas species ATCC 53923 in an aqueous nutrient medium by aerobic fermentation of an assimilable carbon source.

Preferred are those aqueous nutrient media containing inorganic phosphate ions in the range of from about 0.01 to about 1 gram/liter of phosphate.

Preferred uses of the heteropolysaccharide 105-4 are as a thickening or stabilizing agent in a medium containing at least one aqueous liquid phase.

DETAILED DESCRIPTION OF THE INVENTION

The Pseudomonas species producing heteropolysaccharide 105-4 was isolated from a soil sample collected at Guigue (Carabobo) Venezuela.

The heteropolysaccharide produced by Pseudomonas ATCC 53923 is composed principally of carbohydrate with 10–15% by weight substituent acetyl groups. The carbohydrate portion is composed of about 10 to about 25% by weight uronic acid (calculated as glucuronic acid) and mannose, galactose and glucose in the approximate ratio 1.3:1:3.6.

In order to determine the composition of the polysaccharide, purified polymer was obtained by diluting broth twenty-fold with distilled water, removing cells by centrifugation at 18,000×g for 30 min., adding sodium chloride to 0.1% volume and precipitating polymer by addition of 3 volumes isopropanol based on the volume of the diluted polymer solution. The polymer precipitate was removed by filtration through a 100 mesh sieve and washed by repulping in 100 milliliters of 70% isopropanol followed by filtration. Material was collected and dried by lyophilization to constant weight (usually 48 hrs.). Polymer was hydrolyzed either with sulfuric acid or trifluoroacetic acid as follows. Ten milligrams of purified polymer was dissolved in 2 milliliters distilled water with rapid stirring. For hydrolysis with sulfuric acid, 2 ml of 4N sulfuric acid were added and the solution was heated in a sealed glass ampoule at 100° C. for 16 hours. The resulting solution was cooled, neutralized with barium hydroxide, and the pH was adjusted to 5–6 with solid carbon dioxide (dry ice). For hydrolysis with trifluoroacetic acid (TFA), 2 ml of 4M TFA were added and the solution heated in a sealed glass ampoule for 4 hours at 120° C. TFA was removed by evaporation under vacuum at room temperature over sodium hydroxide overnight. Traces of TFA were removed by two cycles of dissolving the residue in distilled water and redrying under vacuum. Neutral sugars and uronic acid were tentatively identified by descending paper chromatography on Whatman 3MM paper. The chromatogram was developed using a solvent system composed of butanol, glacial acetic acid, and water in the ratio 6:4:3. Chromatograms were air dried and treated with a solution prepared by mixing 0.1 milliliter of a saturated aqueous solution of silver nitrate into 20 milliliters of acetone. Sugars and uronic acid react with silver nitrate to give gray to black spots depending on concentration. Spots were identified by chromatography of sugar and uronic acid standards. Locations of spots were consistent with a composition of mannose, galactose, glucose, and glucuronic acid. Sugars in the hydrolysate were further identified and quantitated by gas-liquid chromatography of the alditol acetate derivatives [Hisamatsu et al. Carb. Res., 61, 89 (1978)]. With both hydrolysis procedures (i.e. $H_2SO_4$ or TFA), a ratio of mannose: galactose: glucose: of about 1.3:1:3.6 was obtained. Organic acid substituents of polymer 105-4 were assayed after their removal by mild acid hydrolysis (2N sulfuric acid, 100° C., 60 min) according to the procedure of Hisamatsu supra. Separation was accomplished by isocratic cation exchange chromatography (Biorad Aminex HPX-87H) using a mobile phase of 0.013N $H_2SO_4$, with UV detection at 206 nm. Acetate was the only substituent at about 10 to about 15% by weight of the polymer. Uronic acid was determined by the procedure of Blumenkrantz and Asboe-Hansen, *Anal. Biochem.* 54, 484 (1973). A range of 10–25% (calculated as glucuronic acid) was found.

Polymer 105-4 is extremely effective as a viscosity building agent for aqueous media. Because of this, as well as its pseudoplasticity, compatibility with fresh water, high-salinity water and high-hardness brines, it has utility as a thickening, stabilizing, and suspending agent for a wide variety of applications, including but not limited to liquid detergents, industrial cleaners, sanitizers, fire-fighting aerosols, well drilling and completion fluids, latex paints, and personal care products.

EXAMPLE 1

Fermentation Procedure for Producing Heteropolysaccharide 105-4

A. Culture Maintenance

Pseudomonas Sp. ATCC 53923 grows well on the medium described in Table 1. The same medium, with minor variations as specified below, was sued for fermenter seed preparation and final stage fermentation medium.

TABLE 1

Agar Plate Medium for Culture Maintenance and Culture Purification:

| Glucose | 3% |
|---|---|
| $KH_2PO_4$ | 0.01% |
| Yeast Extract | 0.025% |
| $MgSO_4.7H_2O$ | 0.025% |
| $NH_4NO_3$ | 0.09% |
| $CaCO_3$ | 0.5% |
| Trace metal solution 0.5 ml/ liter medium | |
| Agar | 1.8% |

Trace Metal Stock Solution Composition:

| Ingredient | mg/l distilled water |
|---|---|
| Boric Acid | 285 |
| $MnCl_2.4H_2O$ | 1800 |
| $FeSO_4.7H_2O$ | 1360 |
| Sodium Tartrate | 2098 |
| $CuCl_2$ | 26.9 |
| $ZnCl_2$ | 20.8 |
| $CoCl_2.6H_2O$ | 74.0 |
| $NaMoO_4.2H_2O$ | 25.2 |

The ingredients were dissolved or suspended in distilled water and sterilized by autoclaving for 30 minutes at 121° C. After cooling to 50° C., agar medium was dispensed into Petri pl? lonies of Pseudomonas So. ATCC 53923 grown for 3 days at 30° C were white, raised, and rubbery in consistency.

B. Seed Preparation

The medium was the same as that shown in Table 1 except that agar was omitted and $CaCO_3$ was reduced to 0.3%. Medium was prepared and dispensed (100 milliliters of medium into each 300 ml flask). Flasks were sterilized by autoclaving for 30 minutes at 121° C. After cooling, flasks were inoculated with a loopful of a 3 day old culture from an agar plate. Flasks were incubated at 30° C. with shaking at 200 rpm for 24 hours and 1 ml of the culture was transferred to new Seed Flasks (second stage inoculum) of identical composition and volume which were incubated with shaking at 30° C. for 48 hrs.

C. Fermentation Production Medium

The medium was the same as that shown in Table 1 except that agar and $CaCO_3$ were both omitted and volume was based on inoculated volume of the fermenter as described below. The medium was prepared and dispensed into a 15 liter New Brunswick fermenter as follows. Ingredients for 10 liters of medium (omitting glucose) were prepared in 8.5 liters of distilled water. pH of the medium was adjusted to 8.1 with sodium hydroxide. The fermenter contents were sterilized by autoclaving at 121° C. for one hour. One liter of a 30% glucose solution was sterilized separately at 121° C. for one hour and added aseptically to the fermenter. The fermenter was inoculated with 0.5 liter of inoculum from second stage inoculum. The fermentation temperature was maintained at 30° C. and the air rate was 3 liters/min. pH was maintained between 6.5 and 7.5 during fermentation by addition of sodium hydroxide using a New Brunswick pH controller. The initial agitation rate was 300 rpm, which was raised to 400 rpm and 500 rpm at 24 and 48 hours, respectively. The fermentation was terminated at 72–96 hours. Broth viscosity measured with a Brookfield model LVT viscometer with a #4 spindle at 30 rpm ranged from 9,000 to 14,000 centipoise. The fermenter broth was preserved by adding 3,000 ppm formaldehyde or other appropriate biocide. The polymer concentration as determined by isopropanol precipitation of a preparation clarified to remove cells was 0.8%. The viscosity of a 1425 ppm solution in 500 ppm sodium chloride solution was 1,000 centipoise at 5.1 $sec^{-1}$ using a Fann Viscometer, Model #35A and a B-1 bob with an R-1 rotor.

ATCC Classification

Morphology: This strain is a Gram negative, motile rod. Flagella are polar monotrichous. The colonies on nutrient agar are smooth, entire, and glistening and adhere to the agar. In liquid media a flocculent pellicle is formed at the surface. When grown in nitrogen deficient medium, the cells contain poly-B-hydroxybutyrate inclusions. Fluorescent and pyocyanine pigments are not formed.

Physiology and Biochemistry:

| | | | |
|---|---|---|---|
| Gram positive | − | Starch hydrolysis | + |
| Gram negative | + | Gelatinase | + |
| Gram variable | − | Tween 20 hydrolysis | + |
| Motile at RT | + | Tween 80 hydrolysis | + |
| Flagella peritrichous | − | Indole | − |
| Flagella Lophotrichous | − | Simmons citrate growth | + |
| Flagella monotrichous | + | Urease | + |
| Flagella lateral | − | Nitrate to nitrite | − |
| 4° C. growth | − | Nitrate reduction | − |
| 25° C. growth | + | Nitrite to nitrogen gas | − |
| 30° C. growth | + | Hydrogen sulfide (TSI) | − |
| 37° C. growth | + | Lysine decarboxylase | − |
| 41° C. growth | + | Arginine (Mollers) | − |
| Flourescein produced | − | Ornithine decarboxylase | − |
| Pyocyanine produced | − | Phenylalanine deamination | − |
| Diffusible orange | − | Lecithinase | W |
| Diffusible yellow | − | Phosphatase | + |
| Diffusible purple | − | Catalase | + |
| Non-diffusible green | − | Oxidase | + |
| Other non-diff. pigments | − | Growth on malonate as SCS | + |
| Melanin pigment produced | + | dl-hydroxybuty-rate growth | + |
| pH 6.0 growth | + | PHB accumulation | + |
| 3% NaCl growth | − | Growth on 0.05% cetrimide | − |
| 6.5% NaCl growth | − | Testosterone deg. | − |

-continued

Physiology and Biochemistry:

| | | | |
|---|---|---|---|
| MacConkey agar growth | + | 3-Ketolactose from lactose | − |
| Skim milk agar growth | + | Mucoid growth on glucose agar | + |
| Aesculin hydrolysis | W | Gluconate oxidation | − |
| Casein hydrolysis | + | Growth on acetate as SCS | + |
| | | Tyrosine degradation | + |

W = weakly positive

Oxidative/Fermentative Reactions in Hugh & Leifson's Medium:

| Acid from: | | | |
|---|---|---|---|
| L-arabinose | W | | |
| cellobiose | W | | |
| ethanol | K | | |
| D-fructose | W | | |
| D-glucose Aerobic | W | | |
| D-glucose Anaerobic | − | | |
| Alkaline pH in D-Glucose | − | | |
| glycerol | W | | |
| i-inositol | K | | |
| lactose | K | | |
| maltose | + | | |
| D-mannitol | W | | |
| D-mannose | + | | |
| L-rhamnose | K | | |
| D-ribose | W | | |
| sucrose | K | | |
| trehalose | K | | |
| D-xylose | W | | |
| Control | K | | |
| L-arabinose | + | D-xylose | + |
| cellobiose | + | adonitol | − |
| D-fructose | + | erythritol | − |
| D-glucose | + | glycerol | + |
| lactose | − | ethanol | − |
| maltose | + | geraniol | − |
| D-mannitol | + | i-inositol | − |
| L-rhamnose | − | sebacic acid | + |
| D-ribose | + | acetamide | − |
| D-sorbitol | − | adipate | − |
| sucrose | − | benzoate | − |
| trehalose | − | butyrate | + |
| citraconate | − | glycine | − |
| D-gluconate | + | L-histidine | + |
| M-hydroxybenzoate | − | DL-norleucine | − |
| 2-ketogluconate | − | L-proline | + |
| DL-lactate | + | D-tryptophan | − |
| L-malate | + | L-valine | − |
| pelargonate | − | DL-arginine | − |
| propionate | + | benzylamine | − |
| quinate | − | butylamine | |
| succinate | + | putrescine | |
| L-tartrate | − | mesoconate | − |
| valerate | − | DL-glycerate | − |
| B-alanine | − | L-tryptophan | − |
| D-A-alanine | + | Methanol | − |
| betain | − | | |

+ = acid
− = no change
K = strong alkaline reaction
W = acid on surface but some residual alkaline reaction in body of tube Comments:

Comparison of the characteristics of this strain with ATCC strain data and data from the literature did not result in identification.

The strain resembles *Pseudomonas solanacearum* in its nutritional pattern but not in its biochemical features, particularly casein, starch, and gelatin hydrolysis and nitrate reduction. *P. solanacearum* is described as having 1-4 polar flagella, whereas isolate 105-4 has only one polar flagellum.

EXAMPLE 2

The unusually high viscosities yielded for 0.1 and 1.0% solutions of 105-4 at low shear are illustrated in Table 2 (TDS=Total Dissolved Salts). The highly pseudoplastic or shear-thinning nature of 105-4 solutions, which affords high viscosities at low shear for good solids suspension as well as low viscosities at high shear for ease of mixing and pumping, is shown in FIG. 1. This FIGURE also illustrates the excellent compatibility and thickening prowess of 105-4 with brines of very high salinity and hardness. For each example, solutions were prepared on a Waring ® blender by slow addition of biopolymer into a vortex (maintained by continued adjustment of blender voltage with a rheostat) of the solvent followed by two minutes shear at 50 volts. The viscosities of the resulting solutions were measured on a Haake Buchler Instruments Model RV20 rheometer.

TABLE 2

LOW SHEAR VISCOSITIES OF 105-4 SOLUTIONS
0.1–1% active in 500 ppm TDS brine

| Dosage | Viscosities (cos) at | | |
|---|---|---|---|
| % active | 0.01 | 0.1 | 1 sec$^{-1}$ |
| 0.1% | 1,000,000 | 14,000 | 3,130 |
| 1.0% | >20,000,000 | 770,000 | 90,000 |

EXAMPLE 3

The production of polymer 105-4 was found to be sensitive to phosphate concentration in the fermentation production medium. The results set forth in Table 3 illustrate this sensitivity.

TABLE 3

Effect of Phosphate Concentration on Polymer Production:

| Phosphate Concentration[1] g/l | Polymer Produced (% w/w)[2] |
|---|---|
| 0.07 | 1.31 |
| 0.30 | 0.39 |

[1]As PO$_4$
[2]Fermentation carried out as in Example 1 except phosphate concentration was varied.

I claim:

1. A heteropolysaccharide designated 105-4, said polysaccharide consisting of mannose, galactose and glucose in the approximate molar ratio of 1.3: 1:3.6 and, based on the weight of the polysaccharide, from about 10 to about 25% by weight uronic acid and from about 10 to about 15% by weight acetate groups.

2. A heteropolysaccharide produced by a Pseudomonas having all of the identifying characteristics of ATCC 53923 and designated 105-4, said polysaccharide consisting of mannose, galactose and glucose in the approximate molar ratio of 1.3: 1:3.6, and, based on the weight of the polysaccharide, from about 10–25% uronic acid calculated as glucuronic acid, and from about 10 to about 15% acetic acid groups.

3. A heteropolysaccharide according to claim 2 prepared by a process comprising growing a Pseudomonas having all of the identifying characteristics of ATCC 5393 in an aqueous nutrient medium by aerobic fermentation of an assimilable carbon source.

4. A heteropolysaccharide according to claim 3 wherein the aqueous nutrient medium contains inorganic phosphate ion below 0.5 g/l, production of said heteropolysaccharide sensitive to said phosphate concentration.

5. A heteropolysaccharide according to claim 3 wherein the aqueous nutrient medium contains inorganic phosphate ion below 0.5 g/l.

* * * * *